(12) United States Patent
Wittmer et al.

(10) Patent No.: US 8,499,107 B2
(45) Date of Patent: Jul. 30, 2013

(54) FIELD DEVICE FOR PROCESS AUTOMATION

(75) Inventors: Detlev Wittmer, Maulbronn (DE); Manfred Jagiella, Notzingen (DE)

(73) Assignee: Endress + Hauser Conducta Gesellschaft für Mess- und Regeltechnik mbH + Co. KG, Gerlingen (DE)

(*) Notice: Subject to any disclaimer, the term of this patent is extended or adjusted under 35 U.S.C. 154(b) by 755 days.

(21) Appl. No.: 12/733,280

(22) PCT Filed: Aug. 8, 2008

(86) PCT No.: PCT/EP2008/060430
§ 371 (c)(1),
(2), (4) Date: May 6, 2010

(87) PCT Pub. No.: WO2009/024482
PCT Pub. Date: Feb. 26, 2009

(65) Prior Publication Data
US 2010/0241402 A1 Sep. 23, 2010

(30) Foreign Application Priority Data
Aug. 21, 2007 (DE) .................. 10 2007 039 528

(51) Int. Cl.
G06F 13/12 (2006.01)
G06F 13/38 (2006.01)
G06F 13/00 (2006.01)

(52) U.S. Cl.
USPC .............................. 710/62; 710/33

(58) Field of Classification Search
None
See application file for complete search history.

(56) References Cited

U.S. PATENT DOCUMENTS

| 2006/0206218 A1 | 9/2006 | Glanzer |
| 2007/0011365 A1* | 1/2007 | Jurisch et al. ............. 710/33 |

FOREIGN PATENT DOCUMENTS

| DE | 295 13 552 | 11/1995 |
| DE | 101 61 401 A1 | 6/2003 |
| DE | 102 18 606 | 11/2003 |
| DE | 102 43 781 | 3/2004 |
| DE | 103 13 639 | 10/2004 |
| DE | 10 2004 015 227 | 10/2005 |
| EP | 1 380 907 | 1/2004 |
| EP | 1 550 861 | 7/2005 |
| JP | 1-123512 | 5/1989 |
| JP | 1-164276 | 6/1989 |
| JP | 5-249059 | 9/1993 |
| JP | 10253572 | 9/1998 |
| JP | 2001-190495 | 7/2001 |
| JP | 2005-201900 | 7/2005 |
| WO | WO 03/056423 | 7/2003 |
| WO | WO 2004/049239 | 6/2004 |
| WO | WO 2005/106606 | 11/2005 |

* cited by examiner

*Primary Examiner* — Idriss N Alrobaye
*Assistant Examiner* — Ronald Modo
(74) *Attorney, Agent, or Firm* — Bacon & Thomas, PLLC

(57) ABSTRACT

A field device for process automation, composed of at least two components coupleable with one another, wherein, in each of the components, a control/memory unit is provided, in which, in each case, a parameter set with defined parameters is stored, and wherein, for the case, in which the at least two components are coupled with one another, at least one of the control/memory units reads, and compares with one another, the parameter sets stored in the separate control/memory units of the components, and wherein, in the case of a deviation in the parameter sets, the comparing control/memory unit of the control/memory units makes available, to the components coupled with one another, the intersection of the parameters of the parameter sets.

9 Claims, 1 Drawing Sheet

FIELD DEVICE FOR PROCESS AUTOMATION

TECHNICAL FIELD

The invention relates to a field device for process automation, composed of at least two components coupleable, or coupled, with one another, wherein a control/memory unit is associated with each of the components.

BACKGROUND DISCUSSION

Known from DE 102 18 606 A1 is a potentiometric sensor, which includes a transducer and a digital data memory, wherein the data memory is connected permanently with the sensor. Stored in the data memory are process data or sensor data. The sensor communicates via an interface with a superordinated unit, e.g. a measurement transmitter or a cable. Via the interface, the sensor transmits measurement signals, which represent a pH-value or other measured value. Furthermore, data are read and written, respectively, from and to the data memory via the interface. Preferably, also the energy supply of the sensor occurs via the interface.

Known from DE 103 13 639 A1 is a comparable electrochemical sensor. The electrochemical sensor is, for example, an oxygen sensor. Corresponding sensors with inductive interface and corresponding technology are available from Endress+Hauser in various embodiments under the mark, MEMOSENS.

For the sake of completeness, it is noted that the field device of the invention is not limited to serving only for measuring and monitoring potentiometric or electrochemical, process variables. In principle, the invention is applicable in connection with any field devices, which measure a physical or chemical, process variable.

Problematic in the case of the known solution is that, in connection with the until now unique MEMOSENS technology, in the case of which the plug head and the plug coupling are coupled, or can be coupled, with one another via an inductive interface, in principle, all sensor elements or measurement transmitters of various manufacturers can be connected with the known plug head, or the known plug coupling. For example, any manufacturer of glass electrodes can connect its glass electrodes to the MEMOSENS products. The same is true for the measurement transmitters available from a number of manufacturers.

SUMMARY OF THE INVENTION

An object of the invention is to assure that only authorized, or licensed, manufacturers and suppliers can utilize a defined and unique technology in a defined spectrum.

In order to prevent that non-authorized manufacturers of sensor elements and of measurement transmitters utilize the MEMOSENS technology in connection with their products, two solutions of equal value are provided according to the invention.

A first embodiment of the solution of the invention includes the following features:

In each control/memory unit, a parameter set with defined parameters is stored. As soon as the two components are coupled with one another, at least one of the control/memory units, the so-called comparing control/memory unit, reads and compares the parameter sets stored in the separate control/memory units of the components. In case the parameter sets deviate from one another, the comparing control/memory unit of the control/memory units makes available to the components coupled with one another always the intersection of the parameter of the parameter sets. Thus is assured that the individual components obtain only the minimum, shared functionality.

A second embodiment of the solution of the invention includes the following features:

Each control/memory unit is provided with its own, defined, parameter set, wherein each of the parameter sets is provided with a unique characterizer in the form of a level 0, 1, 2, . . . . In such case, a higher level contains, in each case, the parameters of the preceding level plus additional parameters. For the case, in which the components are coupled with one another, at least one of the control/memory units reads and compares the levels stored in the components. When the levels differ from one another, the parameter set of the component with the lowest shared level is made available to the component, or the components, with a higher level. Also here, the individual components integrated in the measuring system obtain only the minimum shared parameter set, which is associated with each of the components and which is reflected in a defined level.

Relative to the earlier discussed, first solution, the second solution has an important advantage: the comparing control/memory unit requires only the information concerning the level, not, however, the information concerning the parameters, which currently hide behind the level. If, in the course of further development of the field device, additional parameters are added to the already present level, or, even, an additional level is created, then it is sufficient to provide the comparing control/memory unit with the information concerning the level, in which the changed or also the additional parameters are to be placed. Thus, it is possible to omit an updating of the software in the comparing control/memory unit or even in a replacement of the component, in which the comparing control/memory unit is arranged.

An advantageous further development of both solutions of the invention provides that the field device is a measuring device, which is applicable in analytical measurements technology.

Preferably, the components are a plug head for accommodating a transducer, a plug coupling and a measurement transmitter. Field devices, which have this assemblage of components, are available from the assignee under the mark, MEMOSENS. In the MEMOSENS technology, the plug head and the plug coupling can be coupled, or are coupled, with one another via an inductive interface. Of course, the coupling can also be embodied optically or capacitively. An option is, also, to connect the two components of the solution of the invention with one another via a galvanic interface.

In a preferred embodiment of the field device of the invention, the control/memory unit, which performs the comparison of the parameter sets, or the levels, is associated with the plug coupling. The plug coupling is referred to in the context of MEMOSENS-technology often, as well, also as the cable or as the primary side, plug connector element.

In order to illustrate the invention, a concrete example will now be set forth:

The sensor element with plug head is connected via the intelligent cable, i.e. the plug coupling with cable, to a measurement transmitter. For the measurement transmitter, a functionality with the level 0 is licensed. Level 0 is equivalent in meaning with a minimum available functionality. The 'intelligent' cable, which contains the comparing control/memory unit, reads the level from the plug head with sensor element, e.g. level 1, and the level from the measurement transmitter, here level 0. The comparing control/memory unit in the plug coupling, or in the cable, transmits, according to the invention, only the level 0 and, thus, only the parameters classified under the level 0, to the measurement transmitter and to the plug head. According to the invention, always the lowest shared level is ascertained and, respectively, the corresponding functionality freed.

If the same sensor—thus, plug head with sensor element—is operated on a measurement transmitter designed for level 2, the plug coupling, or cable, transmits the level 0 and the level 1. In this case, the level 1 corresponds to the lowest level, which is common to the individual components. The corresponding functionality of level 1 is, thus, freed and made available. The plug coupling works, according to the invention, analogously to a gateway.

In a preferred embodiment of the invention, the parameter set associated with the level 0 contains defined, basic functions. In the case of the parameter set of the level 1, such preferably involves status functions and current status data of the sensor. Associated with the parameter set of the level 2 are diagnostic functions and functions enabling, for example, statements as regards remaining lifetime of the sensor.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
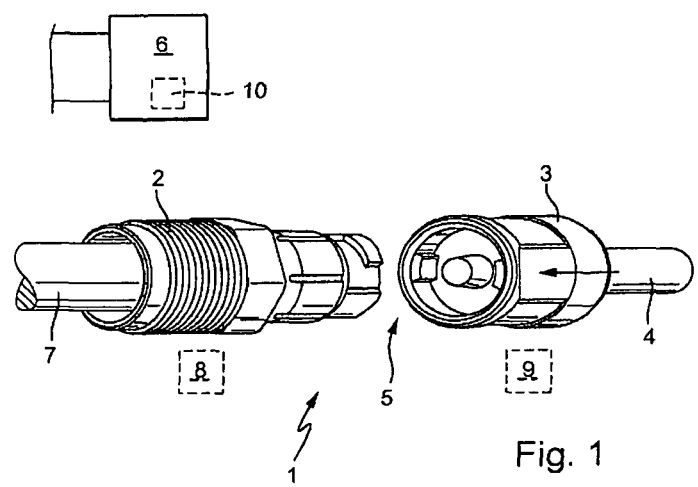
FIG. 1 is a schematic drawing of the individual components of the field device of the invention.

FIG. 1 shows a schematic drawing of the individual components of the field device of the invention 1. The field device of the invention 1 includes three components coupleable, or coupled, with one another: A plug head 3 with a sensor element 4, a plug coupling 2 and a measurement transmitter 6. The measurement transmitter 6 and the plug coupling 2 are connected with one another via a cable 7. Provided in each of the three components, plug head 3, plug coupling 2 and measurement transmitter 6, is a control/memory unit 8, 9, 10. These control/memory units 8, 9, 10 are indicated schematically in FIG. 1.

Figure 1A:
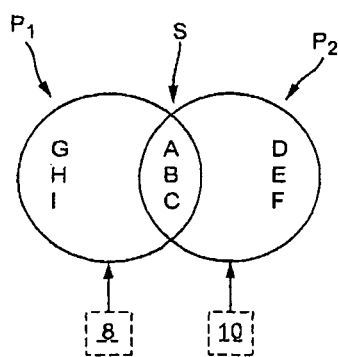
FIG. 1a is a drawing of the intersection of the parameter sets of two components.

For the purpose of avoiding clutter, FIG. 1a shows only the two parameter sets $P_1$, $P_2$, which are stored in the control/memory units 8, 9 of plug head 3 and plug coupling 2. Stored in $P_1$ are the parameters A, B, C, G, H, I; in $P_2$, the parameters A, B, C, D, E, F. If the plug coupling 2, the plug head 3 and the measurement transmitter 6 are coupled with one another, then the comparing control/memory unit 8 (in this case, the comparing control/memory unit 8 is integrated into the plug coupling 2) reads the parameter set $P_2$ stored in the control/memory units 9 of the plug head 3. The parameter set $P_2$ is compared with the parameter set $P_1$, which is stored in the control/memory unit 8 of the plug coupling 2. The control/memory unit 8 compares the two parameter sets $P_1$, $P_2$ with one another. When the parameter sets $P_1$, $P_2$, such as in the illustrated case, deviate from one another, then the comparing control/memory unit 8 of ascertains the matching intersection S of the parameter sets $P_1$, $P_2$ and makes only these available to the additional connected components.

Thus, the individual components 2, 3, 6 receive only the parameters, or the functionality, for which a license is present. Simply stated, the comparing control/memory unit 8 asks the coupled control/memory units 9, 10 the question: What are you permitted to do? Or, which functionalities are licensed to you? Ultimately, the field device 1 composed of a plurality of components 2, 3, 6 receives only the functionalities defined by the intersection S of the functionalities allowed the individual components 2, 3, 6—here, thus, those corresponding to the parameter A, B, C.

Figure 1B:
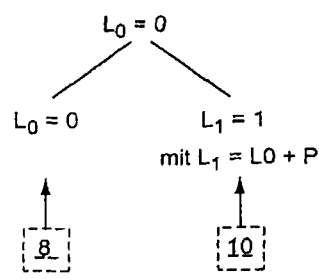
FIG. 1b is an illustration of the ascertaining of the lowest shared level of two components.

FIG. 1b shows an illustration of the ascertaining of the lowest shared level L of two components 2, 3. If the level 0 is associated with the parameters of the plug coupling 2, the licensee has thus obtained only a license for the basic functions, and the plug head 3 with the elementary sensor 4 has the level 1—i.e. the plug head 3 is also able to execute status functions—then the comparing control/memory unit 8 selects the level, which is common to both units 8, 9—thus, the level 0. According to definition, in such case, level 1 contains the parameters of the level 0, plus additional parameters. When connected with the plug coupling 2 and the measurement transmitter 6, sensor 3, 4 is able only to perform basic functions, although it is, on the basis of its stored parameter set, designed also to perform status functions. The license for these additional functions is missing, however, so that functions going beyond the basic functions are locked.

As already set forth above, the use of different levels has the advantage, that it is then sufficient, when, in the course of further development of the field device 1, additional parameters P get added to the already present levels 0, 1, 2, . . . or when even an additional level is newly created, to make available to the comparing control/memory unit 8 the information concerning the level, under which the changed, or also the additional, parameters P are to be classified. Thus, it is possible to omit an updating of the software in the comparing control/memory unit 8 or even a replacement of the component 2, in which the comparing control/memory unit 8 is located.

The invention claimed is:

1. A field device for process automation, comprising:
at least two components coupleable with one another; and
a control/memory unit in each of said components, wherein:
in which, in each case, a parameter set with defined parameters is stored;
for the case, in which said at least two components are coupled with one another, at least one of said control/memory units reads, and compares with one another, the parameter sets stored in said separate control/memory units of the components; and
in case of a deviation in the parameter sets, the comparing control/memory unit of said control/memory units makes available to said components coupled with one another the intersection of the parameters of said parameter sets.

2. The field device as claimed in claim 1, wherein:
the field device is a measuring device applicable in analytical measurements technology.

3. The field device as claimed in claim 1, wherein:
said components are a plug head for accommodating a transducer; a plug coupling and a measurement transmitter.

4. The field device as claimed in claim 3, wherein:
said plug head and said plug coupling can be coupled with one another via a non-galvanic, or a galvanic, interface.

5. The field device as claimed in claim 1, wherein:
said control/memory unit, which performs the comparison of said parameter sets or the levels, is associated with said plug coupling.

6. The field device as claimed in claim 1, wherein:
said parameter set of the level L=0 involves basic functions of the field device.

7. The field device as claimed in claim 1, wherein:
said parameter set of the level L=1 involves status functions, or current status data, of the field device.

8. The field device as claimed in claim 1, wherein:
said parameter set of the level 2 involves diagnostic functions or data permitting estimation of remaining lifetime of the field device.

9. A field device for process automation, comprising:
at least two components coupleable with one another; and
a control/memory unit in each of said components, wherein:
a defined parameter set is associated with each control/memory unit;
each of said parameter sets is provided with a unique characterizer in the form of a level $L_n$ with n=0, 1, 2;
a higher level ($L_{n+m}$) with m=1, 2, 3, contains in each case, the parameters of said lower level ($L_n$) and additional parameters; and
for the case, in which said components are coupled with one another, at least one of said control/memory units reads, and compares with one another, the levels ($L_n$) stored in said components, and, in the case of a deviation, makes available to said component, or components, with a higher level $L_{n+m}$, the parameter set of said component with said lowest level ($L_{min}$).

* * * * *